United States Patent [19]
Martens

[11] Patent Number: 5,297,555
[45] Date of Patent: Mar. 29, 1994

[54] MULTICHANNEL SPECTROMETER

[75] Inventor: Gerhard Martens, Henstedt-Ulzberg, Fed. Rep. of Germany

[73] Assignee: U.S. Philips Corporation, New York, N.Y.

[21] Appl. No.: 803,313

[22] Filed: Dec. 2, 1991

[30] Foreign Application Priority Data

Dec. 7, 1990 [DE] Fed. Rep. of Germany ....... 4039070

[51] Int. Cl.$^5$ .......................... A61B 6/08; G01J 3/18; G01J 3/46
[52] U.S. Cl. ..................... 128/665; 128/633; 250/226; 356/51; 356/229; 356/402
[58] Field of Search ............... 128/633, 665; 356/402, 356/406, 51, 229; 250/226

[56] References Cited

U.S. PATENT DOCUMENTS

| | | | |
|---|---|---|---|
| 3,874,799 | 4/1975 | Isaacs et al. | 356/173 |
| 4,170,987 | 10/1979 | Anselmo et al. | 128/665 |
| 4,241,738 | 12/1980 | Lubbers et al. | 128/666 |
| 4,729,372 | 3/1988 | L'Esperance, Jr. | 606/5 |
| 5,014,707 | 5/1991 | Schwarz et al. | 128/663 |
| 5,014,709 | 5/1991 | Bjelkhagen et al. | 356/347 |

*Primary Examiner*—Lee S. Cohen
*Assistant Examiner*—Krista M. Pfaffle
*Attorney, Agent, or Firm*—Jack D. Slobod

[57] ABSTRACT

The invention relates to a multichannel spectrometer (10), in particular for examining moles (16) having an evaluating and display device (14) and optical means (18, 19, 21, 23, 22) to determine and display reflectance spectra of a skin surface on an ascertainable image plane (x,y) while considering white standards (17). In such a spectrometer for the examination of inter alia malignant moles (16), a contactless optical point-by-point scanning of the skin surface is desirable, which is why the optics of the spectrometer (10) comprise a lens system (18, 21, 22) directed on the skin surface and the white standard (17) and a slotted diaphragm (19) succeeded by a diffraction grating (23) directed in accordance with a slot (20) of the slotted diaphragm (19) for the simultaneous production of the reflectance spectrum of the points of a determinable line (25) of the skin surface and of the white standard (17) on the image plane (x,y) connected to the subsequent diffraction grating (23) with the evaluating and display device (14).

8 Claims, 1 Drawing Sheet

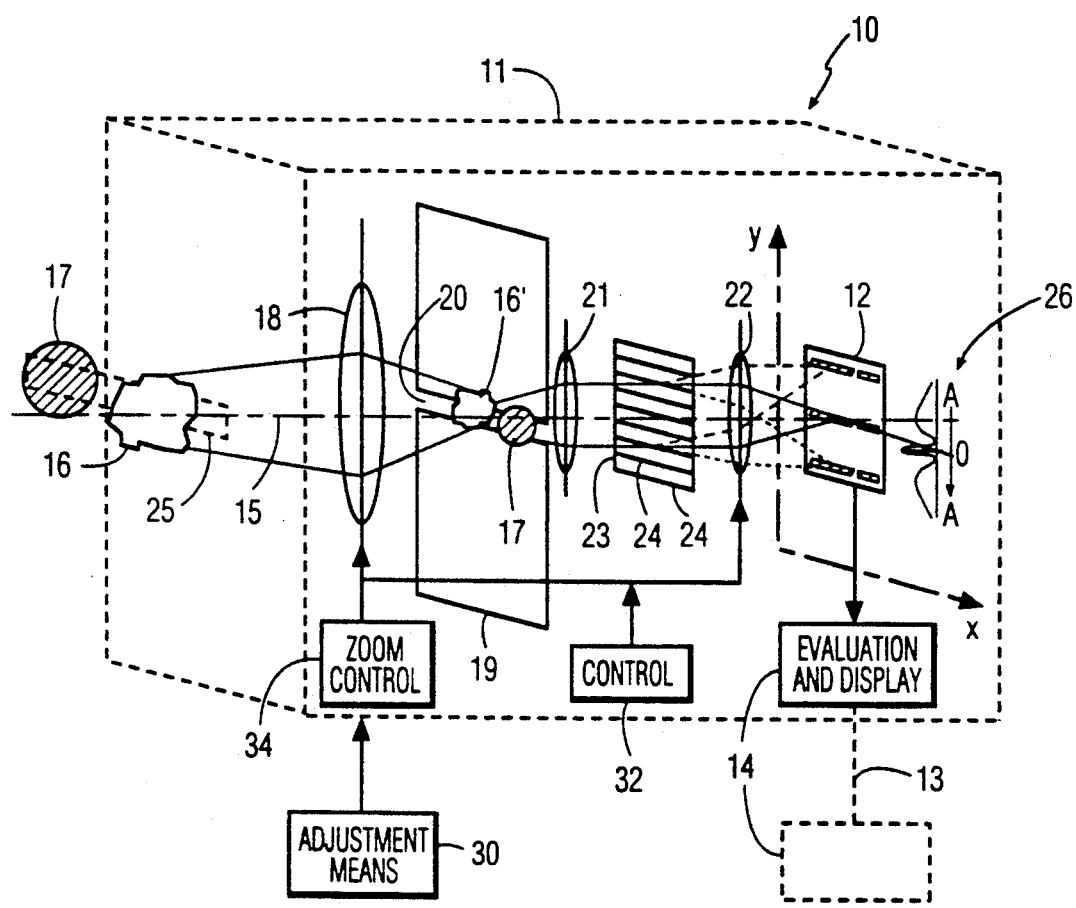

MULTICHANNEL SPECTROMETER

FIELD OF THE INVENTION

The invention relates to a multichannel spectrometer, in particular for examining moles, having an evaluating and display device and optical means to determine and display re-emission spectra of a skin surface in an image plane while considering a white standard.

BACKGROUND OF THE INVENTION

Measurements of body colors become increasingly important in many technological fields. In the medical field it is important to obtain objective standards for body colors, for example, to obtain diagnostic information about the skin surface. In the conventional colors measuring apparatuses, the light which is radiated from the skin surface of a body point is analyzed in its spectrum by a monochromator and is then compared with given standard spectral value curves to determine the color coordinates. In the case of non-self-luminous objects there must be started from a given illumination type or the primary light spectrum must be included and the re-emission spectrum of the body point be corrected thereon.

Such a spectrometer is known from DE-OS 27 26 606 corresponding to U.S. Pat. No. 4,241,738 which relates substantially to a so-called medical spectrophotometer having a spacer ring at the end where the objective is positioned to measure the color by means of the spectrometry of reflected light, so of the measurement of the re-emission (reflectance) of, for example, a skin surface, in which as a reference a white standard is used alternately. Such a spectrometer enables the determination of the re-emission spectrum of a point of the surface.

With structured surfaces, for example, of a skin surface with moles or of the surface of a mole itself, it is necessary not only to determine a defined point with respect to its re-emission spectrum, but also to determine this information of a plurality of skin surface points. In the ideal case it is desirable to determine the re-emission spectrum of each point of the skin surface. This requires an expensive point-by-point scanning of the surface. Furthermore, in the examination of in certain circumstances malignant moles a contact-free examination is desirable.

A device for measuring and evaluating natural fluorescent spectra of organic tissue surfaces is known from DE-OS 38 15 743 corresponding to U.S. Pat. No. 5,014,707. In the latter device it is suggested for establishing the spectral distribution of fluorescent light of the skin surface to expose same to a light stripe by projection of an image of a slot on the skin surface. This has for its result that a common spectrum is obtained, which spectrum is the average of the spectra of all points of the slot image projected from the light source on the skin surface. As already explained hereinbefore, a desired optical point-by-point scanning of the skin surface is not possible with this device.

SUMMARY OF THE INVENTION

It is the object of the invention to provide an optical multichannel spectrometer for the contact-free determination of the various re-emission spectra of the points of at least one line of a skin surface to be examined with constant consideration of a primary light correction.

According to the invention this object is achieved in that the optical means comprise a system of lenses directed on the skin surface and the white standard and a diaphragm succeeded by a diffraction grating aligned with a slot of the diaphragm for the simultaneous production of the re-emission spectrum of the points of a determinable line of the skin surface and of the spectrum of the white standard in the image plane after the diffraction grating and connected to the evaluating and display device.

A preferred embodiment of the invention is characterized in that the system of lenses having an optical axis comprises an objective lens for imaging the white standard and the skin surface on the diaphragm, and a system of two lenses and a diffraction grating arranged between the two lenses for forming a line-shaped image in the image plane. The stripes of the diffraction grating are aligned with the slot of the diaphragm.

A special embodiment of the invention is characterized in that the white standard consists of a tablet of, for example, compressed barium sulphate arranged in at least the stripe of the skin surface. The tablet may be provided, for example, adhered, in a small section on the mole itself or beside it on the skin surface.

For examining the whole surface of the mole on the skin surface it may be advantageous for the multichannel spectrometer according to the invention to be movable and adjustable orthogonally to the slot direction and to the optical axis of the lens system.

According to a particular embodiment, the multichannel spectrometer according to the invention may be further characterized in that it comprises a housing by means of which it may be mounted before a residual-light camera instead of an objective.

The spectrometer according to the invention may be further characterized by a unit for linearly moving the objective lens, or in that the objective lens is a zoom objective.

The arrangement according to the invention of the lens system, the diaphragm and the diffraction grating has for its result that by diffraction of the parallel light beam by the grating the spectra of the individual slot image points are formed in the image plane in two opposite directions starting from the direct slot image of zero order and at right angles to the direction of the slot. The correction, i.e. the standardization of the re-emission spectra of, for example, the mole with respect to the spectral distribution of the primary light occurs via the re-emission spectrum of the white standard which spectrum is also determined, which is why substantially any primary light may be used, so long as the stripe is illuminated.

According to a particular embodiment of the invention a two-dimensional detector is provided in the image plane for the detection of the spectra of the individual points of a stripe of the skin surface and simultaneously of the white standard, to finally compute and display the color coordinates for each point of the stripe in question by means of a succeeding evaluating and display device. The calculation is done for each point of the stripe from the standardized reflectance spectra and tabulated standard spectral value curves which may be stored in a store of the evaluating device.

So by means of the multichannel spectrometer according to the invention a stripe-shaped section from the surface, for example, of a mole, may be spectrometrized for each point simultaneously without contact. For scanning the complete surface it is necessary only that the spectrometer can be moved accordingly. However, for diagnostic purposes it is often sufficient to know the color profile of, for example, one line.

BRIEF DESCRIPTION OF THE DRAWING

An embodiment of the invention is shown in the sole FIG. 1 and will be described in greater detail hereinafter.

DESCRIPTION OF THE PREFERRED EMBODIMENT

The figure shows the principle construction and the operation of the multichannel spectrometer 10 which is accommodated in a housing 11 and comprises a two-dimensional detector 12 which via a connection line 13 is connected to an evaluating and display device 14 which, for example, is arranged outside (broken lines) the housing 11. The evaluating and display device 14 (solid lines) may also be accommodated in the housing 11.

The optical axis 15 of the multichannel spectrometer 10 is directed on a skin surface outside the housing 11 and in particular on a mole 16 present on the skin surface. A sample of compressed barium sulphate, for example, in the form of a tablet, is connected as a white standard 17 beside the mole 16 on the skin surface not shown. The white standard 17 may alternatively be provided on or partly on the mole 16 but does not cover it substantially. The mole 16 and also the white standard 17 on the skin surface is subjected to wide-band spectral exposure by a light source, not shown. However, narrow-band spectral exposure is also possible. The exposure of an evaluated section or the evaluated stripe 25, must be uniform throughout the section.

By means of an objective lens 18 which may, for example, be movable via control 34 and is present in the housing 11, the mole 16 and the white standard 17 are simultaneously displayed sharply in the slot 20 area of a diaphragm 19 at 16' and 17', respectively. For that purpose the spacing between the objective lens 18 and the slot 20 in the direction of the optical axis 15 may be controlled by a device such as control 32 for linear movement. The objective lens 18 may also be a zoom lens having a control 34. Different magnifications may then advantageously be adjusted without the spacing between the spectrometer and the skin surface having to be varied. The diaphragm 19 comprises the slot 20 which extends horizontally in the plane of the drawing and allows only a stripe-shaped section 25 of the skin surface, i.e. of the mole 16 and of the white standard 17, to pass.

Via a system of two lenses 21 and 22 succeeding the diaphragm 19 the stripe-shaped intermediate image is projected in an image plane x, y. In the image plane x, y which succeeds the double lens system of the lenses 21 and 22, the two-dimensional optical detector 12 is provided. A diffraction grating 23 whose stripes 24 extend parallel to the direction of the gap 20 of the diaphragm 19 is provided between the lenses 21 and 22. The double lens system of the lenses 21 and 22 is provided between the diaphragm 19 and the detector 12 in such a manner that the front focus of the lens 21 lies in the plane of diaphragm 19 and the rear focus of the lens 22 lies in the image plane x, y. The parallelism of the light beam in the double lens system is hence determined by the spacing between the lens 21 and the diaphragm 19. This means that it is necessary for the front focus of lens 21 to lie exactly in the plane of the diaphragm 19. For the detector 12 and the lens 22 it holds that the rear focus of the lens 22 lies exactly in the image plane x, y, so in the plane of the detector 12.

The parallel light beam from the intermediate image of lens 21 is diffracted by the diffraction grating 23 in a direction orthogonal to the direction of the gap 20 and to the optical axis 15. This has for its result that in the image plane x, y, i.e. on the two-dimensional detector 12, the spectra of the individual gap image points also extend orthogonally to the gap image, namely starting from the direct gap image of zero order in two opposite directions. This is illustrated by the dotted lines in the Figure on the detector 12 and by a diagram 26. This latter is shown in the correct position beside the detector 12 for clarity.

The correction, i.e. the standardization of the re-emission spectra of the mole 16 with respect to the spectral distribution of the primary light, occurs via the re-emission spectrum of the white standard 17 which spectrum is also determined, as is indicated by dotted lines on the detector 12. The calculation of the color coordinates is carried out in the evaluating device of the evaluating and display device 14 for each point of the stripe 25 of the mole from the standardized reflectance spectra and tabulated standard spectral value curves which are stored in a store of the evaluating device. The evaluating device may be a microprocessor.

As already stated, the housing 11 may advantageously be constructed in a manner similar to a camera objective, so that the multichannel spectrometer can be mounted instead of an objective in front of a low-light-level camera by means of which the spectra can be detected and be passed on to the evaluating and display device 14.

The multichannel spectrometer may be provided with a such as adjustment means 30 for moving, so raising and lowering, respectively, the multichannel spectrometer, so as to evaluate several lines 25 of a mole. Such device may, for example, comprise a normal camera tripod.

The characteristic features of the invention as disclosed in the specification hereinbefore, the drawing as well as the claims, may be applied both individually and in any combination for realizing the various embodiments according to the invention.

I claim:

1. A spectrometer for analyzing radiation re-emitted from a skin surface under examination, in relation to a white standard, said spectrometer comprising;

a detector having an image plane, which detector is for producing signals in response to radiation projected onto said image plane;

optical means for, in response to re-emitted radiation from points in a stripe-shaped region of said skin surface under examination, projecting said re-emitted radiation onto said image plane as an elongated image formed on said image plane, said optical means including a diaphragm having a slot through which at least a portion of the re-emitted radiation passes, which slot is elongated in a direction to define a direction of elongation of said stripe-shaped region and of said image, and a diffraction grating for receiving at least a portion of the re-emitted radiation passing through said slot for causing diffraction of the received re-emitted radiation, based on color content, in a direction in the image plane which is orthogonal to the direction of image elongation; and evaluating and display means, responsive to signals generated by the detector, for simultaneously producing from said image formed in said image plane, individual re-emission spectra for a plurality of said points.

2. A spectrometer as claimed in claim 1, wherein the detector comprises a residual light camera.

3. A spectrometer as claimed in claim 1, including means for adjusting the optical means for varying the width of the stripe-shaped region.

4. A spectrometer as claimed in claim 1, said optical means further comprising an objective lens, for location in an optical path between the skin surface under examination and the diaphragm, and a system of first and second lenses, the first lens being in an optical path between the diaphragm and the diffraction grating and the second lens being in an optical path between the diffraction grating and the image surface.

5. A spectrometer as claimed in claim 1, wherein the evaluating and display means further produces a white standard spectrum from measurement of radiation re-emitted from a white standard object.

6. A spectrometer as claimed in claim 5, wherein said white standard object is adapted for placement on a portion of the stripe-shaped region of said skin surface under examination such that radiation re-emitted from said object is projected onto said image plane by said optical means.

7. A spectrometer as claimed in claim 1, further comprising means for moving the optical means relative to the input plane in a direction orthogonal to the direction of slot elongation for examining different stripe-shaped regions of said skin surface under examination.

8. A spectrometer as claimed in claim 1, wherein the evaluating and display means further comprise means for calculating color coordinates for each of said points by using standard spectral value data stored in said evaluating and display means.

* * * * *